(12) United States Patent
Biehl et al.

(10) Patent No.: US 11,090,479 B2
(45) Date of Patent: Aug. 17, 2021

(54) VALVE UNIT FOR AN INSTALLATION FOR PRODUCING A MEDICAL PREPARATION

(71) Applicant: FRESENIUS KABI DEUTSCHLAND GMBH, Bad Homburg (DE)

(72) Inventors: Martin Biehl, St. Wendel (DE);
Michael Hock, Münzenberg (DE);
Henrik Schaake, Bad Homburg (DE);
Marcel Borgward, Neuenstadt/Stein am Kocher (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 209 days.

(21) Appl. No.: 15/998,626

(22) PCT Filed: Feb. 17, 2017

(86) PCT No.: PCT/EP2017/053626
§ 371 (c)(1),
(2) Date: Aug. 16, 2018

(87) PCT Pub. No.: WO2017/140849
PCT Pub. Date: Aug. 24, 2017

(65) Prior Publication Data
US 2019/0262234 A1    Aug. 29, 2019

(51) Int. Cl.
*A61M 39/22* (2006.01)
*A61J 3/00* (2006.01)
*F16K 27/00* (2006.01)
*F16K 11/076* (2006.01)
*F16K 11/085* (2006.01)
(Continued)

(52) U.S. Cl.
CPC ............ *A61M 39/223* (2013.01); *A61J 3/002* (2013.01); *B65B 3/003* (2013.01); *B65D 83/68* (2013.01); *F16K 11/076* (2013.01); *F16K 11/0853* (2013.01); *F16K 27/003* (2013.01); *A61J 1/2062* (2015.05); *A61J 15/0092* (2013.01); *Y10T 137/86823* (2015.04); *Y10T 137/87692* (2015.04)

(58) Field of Classification Search
CPC .. F16K 11/076; F16K 11/0853; F16K 27/003; Y10T 137/87692; Y10T 137/86823; A61M 39/223; B65D 83/68; A61J 1/2062; A61J 3/002
See application file for complete search history.

(56) References Cited

U.S. PATENT DOCUMENTS 3,647,118 A    3/1972 Johnson
4,116,364 A *  9/1978 Culbertson ................ B01J 4/00
                                             222/40

(Continued)

FOREIGN PATENT DOCUMENTS

CN    2189466 Y    2/1995
CN    202143730 U  2/2012
(Continued)

*Primary Examiner* — Atif H Chaudry
(74) *Attorney, Agent, or Firm* — Occhiuti & Rohlicek LLP

(57) ABSTRACT

The invention relates to a valve unit for a system for producing parenteral nutrition, in which unit a three-way valve is used for each pair of connections to a source container. The valve unit is a component that can be mounted on die system and removed again after use. The valve unit is in particular provided as an interchangeable disposable component.

19 Claims, 14 Drawing Sheets

(51) Int. Cl.
*B65D 83/68* (2006.01)
*A61J 1/20* (2006.01)
*A61J 15/00* (2006.01)
*B65B 3/00* (2006.01)

(56) References Cited

U.S. PATENT DOCUMENTS

| | | | | |
|---|---|---|---|---|
| 4,447,230 | A | * | 5/1984 | Gula .................. A61M 5/1408 |
| | | | | 604/122 |
| 4,559,036 | A | * | 12/1985 | Wunsch ............ A61M 5/16827 |
| | | | | 604/81 |
| 4,718,467 | A | | 1/1988 | Di Gianfilippo |
| 5,037,390 | A | * | 8/1991 | Raines ................... A61J 3/002 |
| | | | | 604/83 |
| 5,313,992 | A | * | 5/1994 | Grabenkort ............ A61J 3/002 |
| | | | | 137/565.29 |
| 5,431,202 | A | | 7/1995 | Dikeman |
| 5,445,180 | A | | 8/1995 | Divall |
| 2009/0065724 | A1 | * | 3/2009 | Mitton ................... B01F 5/008 |
| | | | | 251/209 |
| 2016/0310362 | A1 | * | 10/2016 | Lane .................. B01F 13/1055 |

FOREIGN PATENT DOCUMENTS

| CN | 104 161 677 | | 11/2014 |
|---|---|---|---|
| JP | H07100212 | A | 4/1995 |
| JP | 3225366 | B2 | 11/2001 |

* cited by examiner

VALVE UNIT FOR AN INSTALLATION FOR PRODUCING A MEDICAL PREPARATION

CROSS REFERENCE TO RELATED APPLICATIONS

This application is the national phase under 35 USC 371 of international application no. PCT/EP2017/053626, filed Feb. 17, 207, which claims the benefit of the priority dates of European Application No. 1615629.6 filed Feb. 19, 2016, European Application No. 16156531, filed Feb. 19, 2016, European Application No. 16173695.4, filed Jun. 9, 2016, and European Application No. 16173696, filed Jun. 9, 2016. The contents of the aforementioned applications are incorporated herein by reference in their entireties.

TECHNICAL FIELD

The invention relates to a valve unit for a installation for producing a medical preparation. The invention relates in particular to a valve unit for a installation by way of which, for example, infusion pouches or syringes for parenteral nutrition are filled.

BACKGROUND TO THE INVENTION

Installations for producing a medical preparation, in particular for producing a preparation for parenteral nutrition, are used, for example, in pharmacies or hospitals in order for a patient-specific preparation, in particular a mixture from various basic nutrients, trace elements, and vitamins, optionally also conjointly with a medication, to be filled.

Installations of this type are also referred to as TPN compounders (TPN=total parenteral nutrition). Installations are known in practice and commercially available such as, for example, the MultiComp® installation by the Fresenius company comprise a computer-controlled pump unit by way of which the component parts of the composition are transferred from different source containers into a target container that is located on a balance.

At least in the case of a separate pump not being available for each source container, it is necessary for the metering from different source containers to be controlled by way of valves.

It is disadvantageous that the provision of valves is complex. Because of the poor cleaning capability of reusable valves, the latter are not considered in most instances.

OBJECT OF THE INVENTION

By contrast the invention is based on the object of providing a valve unit for an installation for producing a medical preparation, said valve unit being designed in a simple and compact manner and in particular also being able to be provided in a sufficiently cost-effective manner as a single-use component, thus as a so-called disposable item.

SUMMARY OF THE INVENTION

The object of the invention is already achieved by a valve unit according to one of the independent claims.

Preferred embodiments and refinements of the invention can be derived from the subject matter of the respective dependent claims, from the description, and from the figures.

The invention relates to a valve unit for an installation for producing a medical preparation. In particular, the valve unit can be fastened to the installation and removed again after use.

The invention relates in particular to a valve unit for an installation for preparing parenteral nutrition, thus an installation by way of which ingredients from different source containers in a patient-specific composition are supplied to a target container.

The valve unit comprises a housing having a plurality of inflows, wherein the inflows are connectable to an outflow by way of valves. The Largest container is filled by way of the outflow.

The valve unit is configured in particular as a replaceable single-use component, preferably in the manner of a cartridge, wherein the valves have engagement means for the mechanical activation for opening and closing.

The valves sitting in the housing by way of these engagement means which are configured in particular as slots can be opened and closed or (in more general terms) activated by a motor present in the installation.

During the operation of the installation always only one valve is thus typically opened at any one time, such that liquid can be retrieved from only one source container. The different component parts from different source containers are thus repeatedly transferred by way of the different inflows into the target container in order for the latter to be filled.

According to the invention, the valves are configured at least as 3-way valves. It has been demonstrated that a valve unit of this type can be implemented in a simple and compact design by using 3-way valves. The way valve comprises at least two inflows and one outflow such that two source containers can be connected to a single valve.

In particular, valves which are configured as 3/3-way valves having a blocked position, preferably a blocked central position, are used. A single valve can thus open and close the inflows from two source containers.

The valves are preferably configured as plug valves.

In the case of one embodiment of the invention the valves are disposed in at least two, preferably straight, rows. The valves that are present in the rows are preferably disposed so as to be mutually offset. A valve of one row is preferably disposed so as to be centric in relation to the opposite valves of the other row.

When viewed in a plan view of the valve unit, the valves, and thus the engagement means for mechanical activation, thus do not form an arrangement in which imaginary straight lines that connect the valves intersect in an orthogonal manner.

Rather, the valves and thus the engagement means for mechanical activation are preferably disposed according to the principle of the hexagonally tightest pack, but so as to be mutually spaced apart.

The valves can thus be assembled in a tighter manner which likewise enables a more compact design embodiment. This results in particular in a reduced volume of the valve unit and thus in a reduce dead volume.

By contrast, the inflows of the valves can be disposed in rows, wherein the inflows (with the exception of peripheral inflows) sit in each case directly or substantially directly opposite the inflows of the opposite row.

The valves preferably are adjacent to a duct in the housing of the valve unit, wherein an opening is present between the duct and an outlet of the valve. The duct laterally preferably has openings that lead to the valves.

The opening can in each case be implemented in that, for example, the valve housing has a rotationally symmetrical shape within which the plug of the valve can rotate. The valve housing is preferably configured so as to be substantially circular-cylindrical. This circular-cylindrical shape in a view from the top overlaps the duct such that the opening and thus the outlet of the three-way valve is configured at the overlapping position.

The duct in turn is connected to the outflow of the valve unit which serves for filling the target container.

The duct at least in the region of the valves preferably has a consistent diameter. This leads the valves which are preferably embodied in an identical manner to also be connected to the duct by means of an opening of identical size, this in turn ensuring an identical flow rate or flow resistance of the different valves in the open state.

The housing of the valve unit is preferably configured as an injection-molded component.

The housing can in particular have a cuboid basic shape.

In the case of one embodiment of the invention the base of the housing is open and serves for receiving the drive means on the installation once the housing has been placed onto the installation.

The valves, in particular valve housings which serve for receiving the plugs can be part of a plate of the housing.

A duct having a consistent cross section in the housing in the case of an injection-molded component can be implemented in one embodiment of the invention in that two housing component parts, an upper and a lower housing half, are placed on top of one another, wherein the duct is configured between these housing halves.

In the case of another embodiment of the invention the duct is disposed in an integrally configured housing portion, in particular in an integrally configured housing.

The valve unit is preferably provided for single use as a so-called disposable item. Single use is understood to be a design embodiment of the valve unit in which it is not provided that said valve unit is cleaned and re-used.

In the case of one refinement of the invention the inflows of the valve unit comprise in each case one hose, wherein hoses are or can be present in at least two diameters.

It is provided in particular for the hoses of source containers for so-called micro-quantities thus, for example, preparations which comprise trace elements or vitamins and which are supplied in a minor dosage, to be designed having a smaller diameter than those hoses by way of which the main component parts, for example sugar solutions, fatty acids, amino acids, are metered.

A comparatively thin hose can in particular have less than at least half the internal diameter of the larger hose.

In the case of one embodiment it is provided that hoses having dissimilar length are used. It is in particular provided that the comparatively thick hoses for metering the main component parts of the preparation are configured so as to be longer. Comparatively large source containers can thus be suspended from a more remote position of the installation, for example from a bar. Comparatively small source containers can be disposed closer to the valve unit, this further reducing the remaining residual quantities of these often expensive preparation component parts when the valve unit is replaced.

The valve unit preferably comprises at least four, particularly preferably at least eight, most particularly preferably twelve, inflows.

The valve unit can be fastened on top of the installation. The housing of the valve unit can in particular comprise latching means in order to be readily fastened on top of the installation.

After the installation has been used, the valve unit can be removed from the installation again and preferably be replaced by a new valve unit. The aforementioned latching means in this variant are therefore designed so as to be releasable. The latching means are preferably releasable when viewed from one side of the valve unit such that the latching mechanism can be released from the front, for example, and the valve unit can be easily removed. This can be implemented, for example, by a collar that engages below a form-fitting element on the installation and by a sprung latching hook on the opposite side of the valve unit.

In the case of one embodiment of the invention the valve unit comprises valves having plugs from an elastomer, said plugs being inserted into the housing preferably in a lubricant-free manner.

The plugs preferably have a Shore A hardness of 60 to 100, preferably of 70 to 90, particularly preferably of 80 to 85. The plugs in one embodiment are provided by a thermoplastic elastomer. This in a first example is a urethane-based thermoplastic elastomer. This can furthermore be a cross-linked olefin-based thermoplastic elastomer provided, for example, by EPDM rubber particles that are enclosed in a PP matrix.

It has been demonstrated that a positive sealing effect can be achieved in a very simple manner by way of plugs that are configured so as to be substantially circular-cylindrical and that are press-fitted into a valve housing that is configured so as to be circular-cylindrical.

The plugs preferably on a lower side have an engagement element, in particular a slot, by way of which the plugs by way of a motor of the installation can be activated by way of a valve control unit that is present as part of the installation.

The valve unit, besides the hoses and the connectors of the latter, can be composed of only the housing and the plugs that are inserted into the housing, and is thus configured in a simple manner from few components.

It has furthermore been demonstrated that a plug that is configured so as to be substantially circular-cylindrical, and that for opening a duct has a clearance in the jacket, by the movement of the clearance on the opening toward the duct is self-centering or self-positioning in the axial direction. It is not necessary for the plugs to be fixed by way of a form-fitting element such as, for example, a plate having an opening.

The valve housing on the upper side thereof is preferably at least partially closed such that the plug has a detent in the insertion direction. This prevents the plug from penetrating the valve housing when the valve unit is being assembled. Once the valve unit has been placed onto the installation in a manner according to the intended use, the plug is thus positionally secured in one direction by the detent and in the other direction by engagement means of the motorized drive of the installation.

In the case of one refinement of the invention the outflow of the valve unit is connected to a hose which comprises at least three portions, wherein a central portion has a cross section that is enlarged in relation to the adjacent portions.

It is in particular provided that the hose present on the outflow is used for a peristaltic pump, in particular for a hose pump, for example a roller pump or a finger pump, wherein the central portion is inserted into the pump. The medium in the case of pumps of this type is conveyed by periodically squeezing a hose. The enlarged cross section of the central hose portion is chosen such that said cross section can be used for the peristaltic pump used. The cross sections of the two other hose portions are preferably configured for the volumetric flows required.

The entire distance from the source container up to the connector of the target container is thus configured as a single-use component. There are no components, for example parts of a pump, that come into contact with the media being transferred.

The invention furthermore relates to a valve unit for an installation for producing a medical preparation, in particular a valve unit having one or a plurality of the aforementioned features.

The valve unit likewise comprises a housing having a plurality of inflows, wherein the inflows are connectable to an outflow by way of valves.

According to the invention, the valves comprise plugs which are inserted into the housing, wherein a fluid in an opened position is capable of being guided past on the external face of the plugs.

According to the invention, the external face of the plugs thus serves as a sealing face, or the fluid in the opened state is guided along the external face of the plugs.

The plugs are preferably embodied so as to be circular-cylindrical and in the jacket comprise at least one clearance by way of which in an opened position the duct between the inflow and the outflow of the valve is released. The plugs preferably have two opposite clearances. In each case one clearance is assigned to each of the opened positions.

The valves are preferably only press-fitted into the valve housings which are configured in the housing of the valve unit.

In the case of one refinement of the invention the plugs, which are preferably configured from an elastomer, comprise at least one encircling web above and below the clearance, said web configuring a lip seal in relation to the housing.

Preferably at least two, and particularly preferably at least three, webs that are axially mutually spaced apart are provided.

The valve unit is sealed in relation to the exterior by way of said webs. The webs furthermore facilitate the press-fitting of the plugs since the material of the webs can yield in a lateral manner.

In the case of one refinement of the invention it is provided that the plug, in particular in a manner adjacent to the clearance, has webs that run in the axial direction. Said webs serve as lip seals of the valve in the closed position of the latter, or as sealing means in relation to the respective duct that is not opened.

According to a further aspect of the invention, the inflows of a valve unit comprise in each case one hose which is inseparably connected, for example by welding or adhesive-bonding, to the housing.

An inseparable connection is understood to be a connection which in the intended use cannot be released in a non-destructive manner.

This simplifies the use of the valve unit since the user does not have to connect any hoses. The safety is also enhanced since there are no connectors that can be confused, on the one hand, and individual hoses cannot be used multiple times in an impermissible manner, on the other hand.

The valve unit is connected to the source containers by way of the hoses. Said valve unit is provided for filling, for example, a specific volumetric quantity into a plurality of target containers, or for use over a specific temporal period.

After a predefined volume has flown through and/or after a predefined temporal period has expired, the valve unit is removed and replaced by a new valve unit.

The outflow of the housing is also preferably inseparably connected to a hose by way of which the preparation is transferred into a target container.

BRIEF DESCRIPTION OF THE DRAWINGS

The subject matter of the invention is to be explained hereunder with reference to an exemplary embodiment and by means of the drawings FIGS. 1 to 14, in which.

The opening positions and the closing position of a valve are to be explained with reference to the sectional illustrations according to FIGS. 7a to 7c and FIGS. 8a to 8c.

Figure 9:
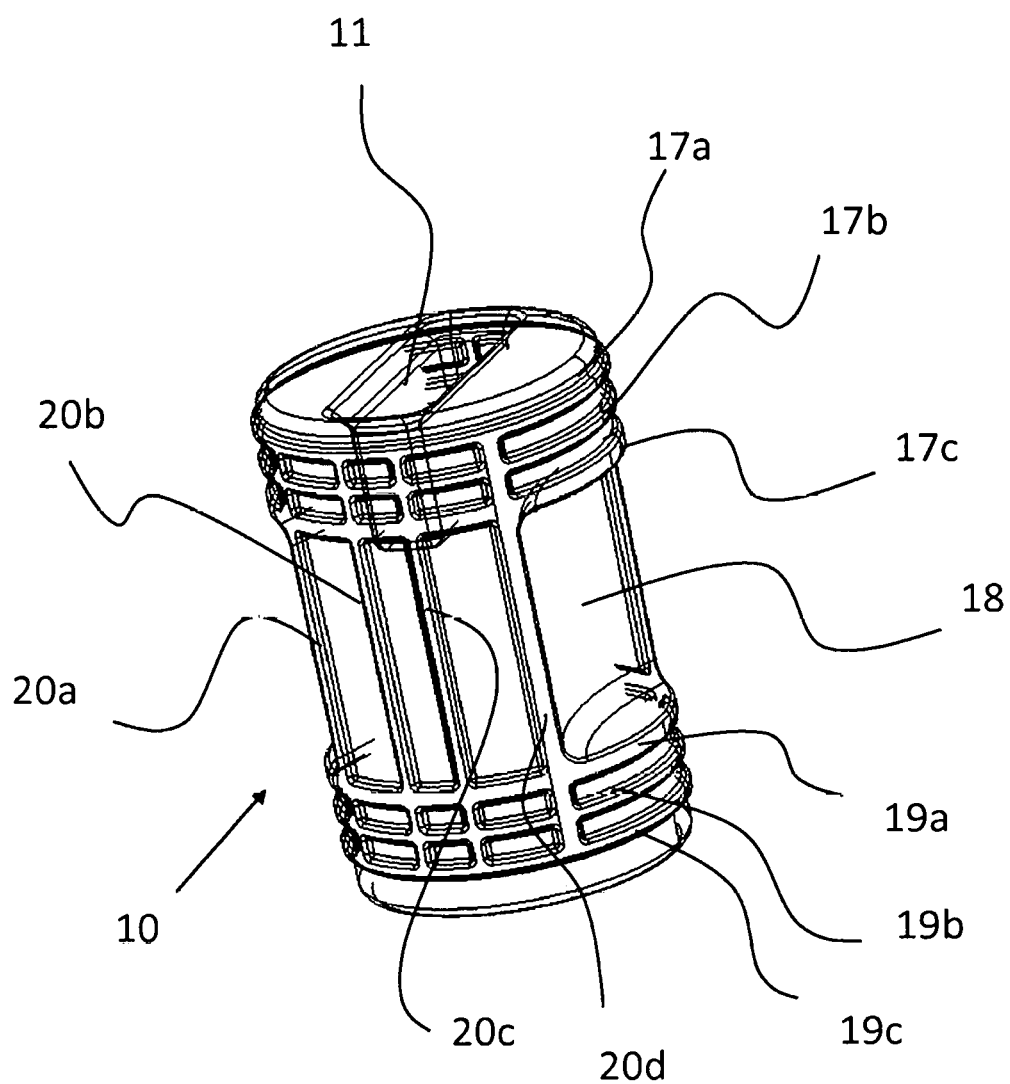
Figure 10:
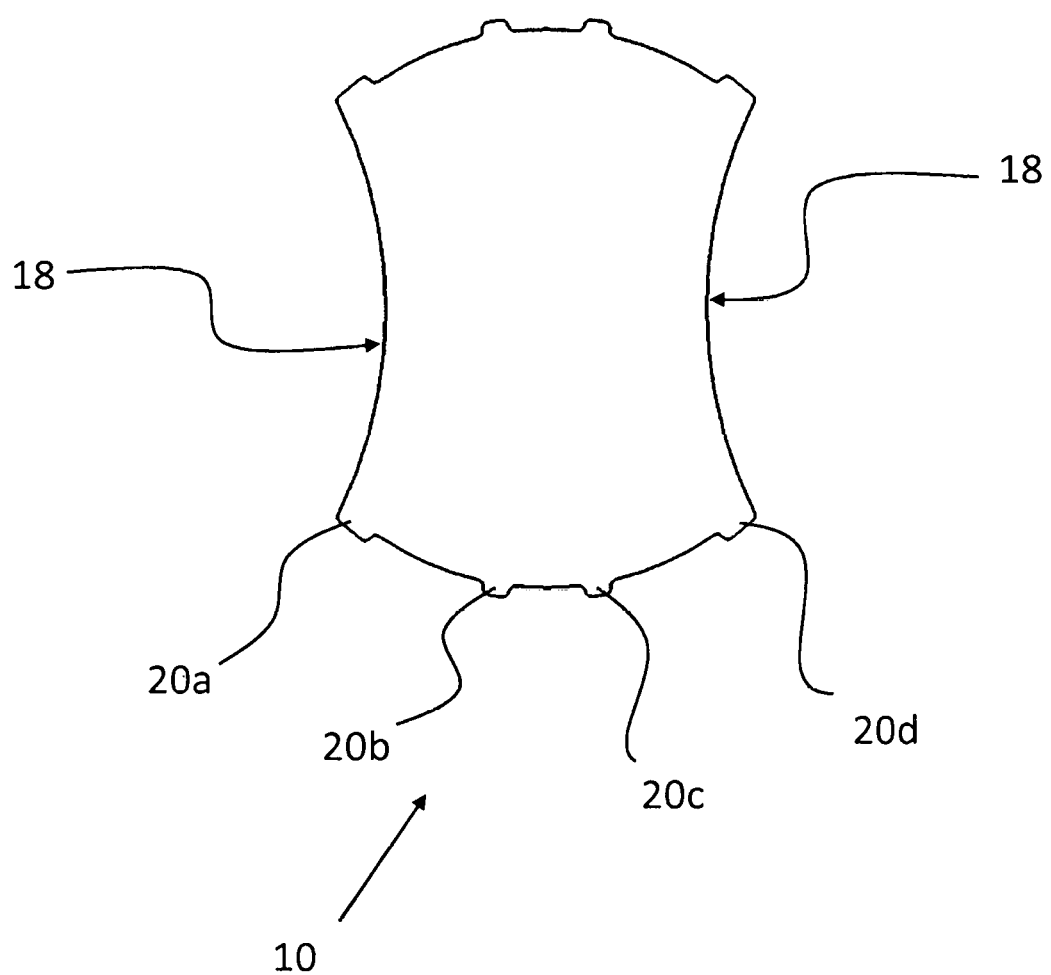
Figure 11:
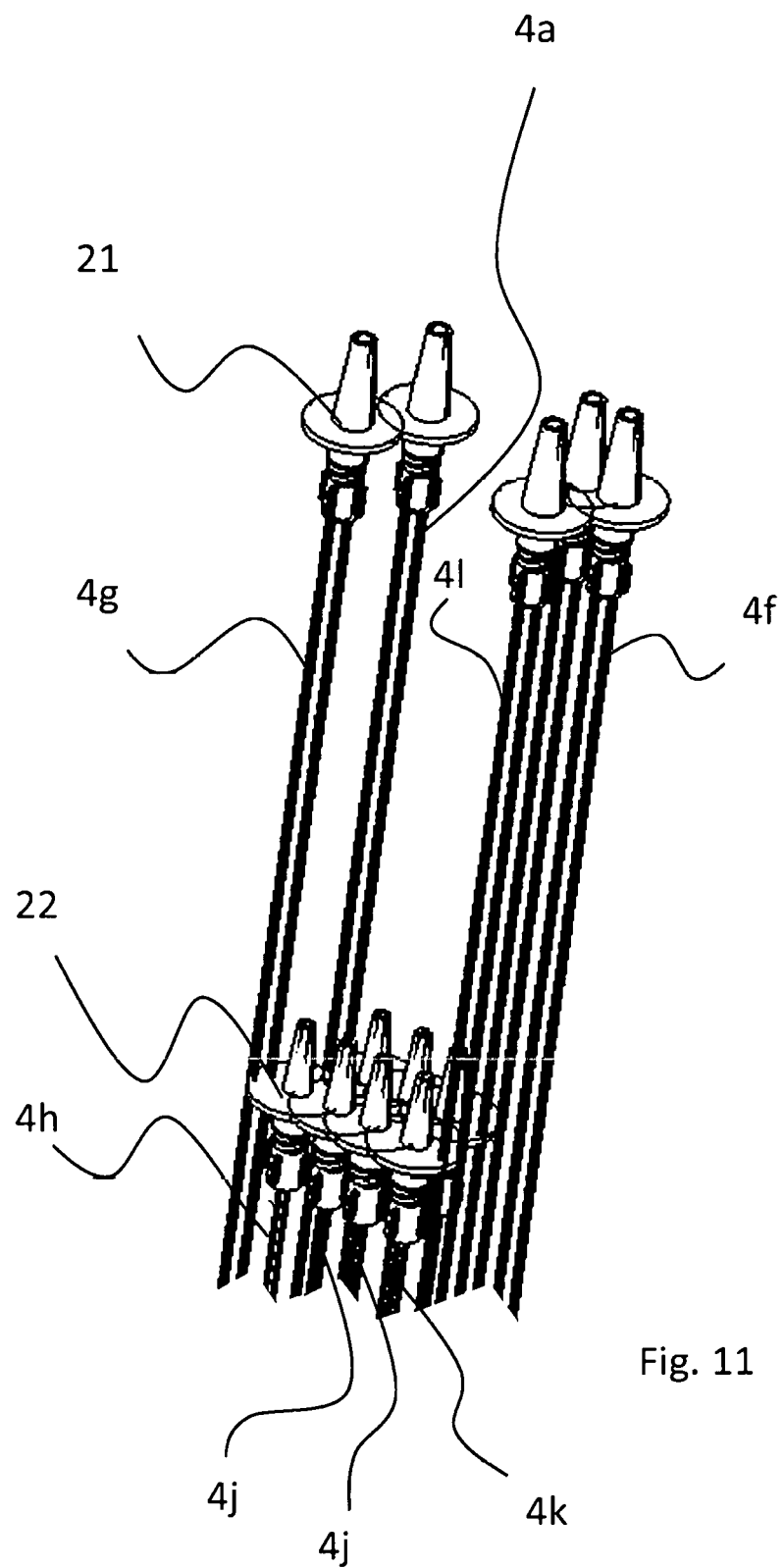
Figure 12:
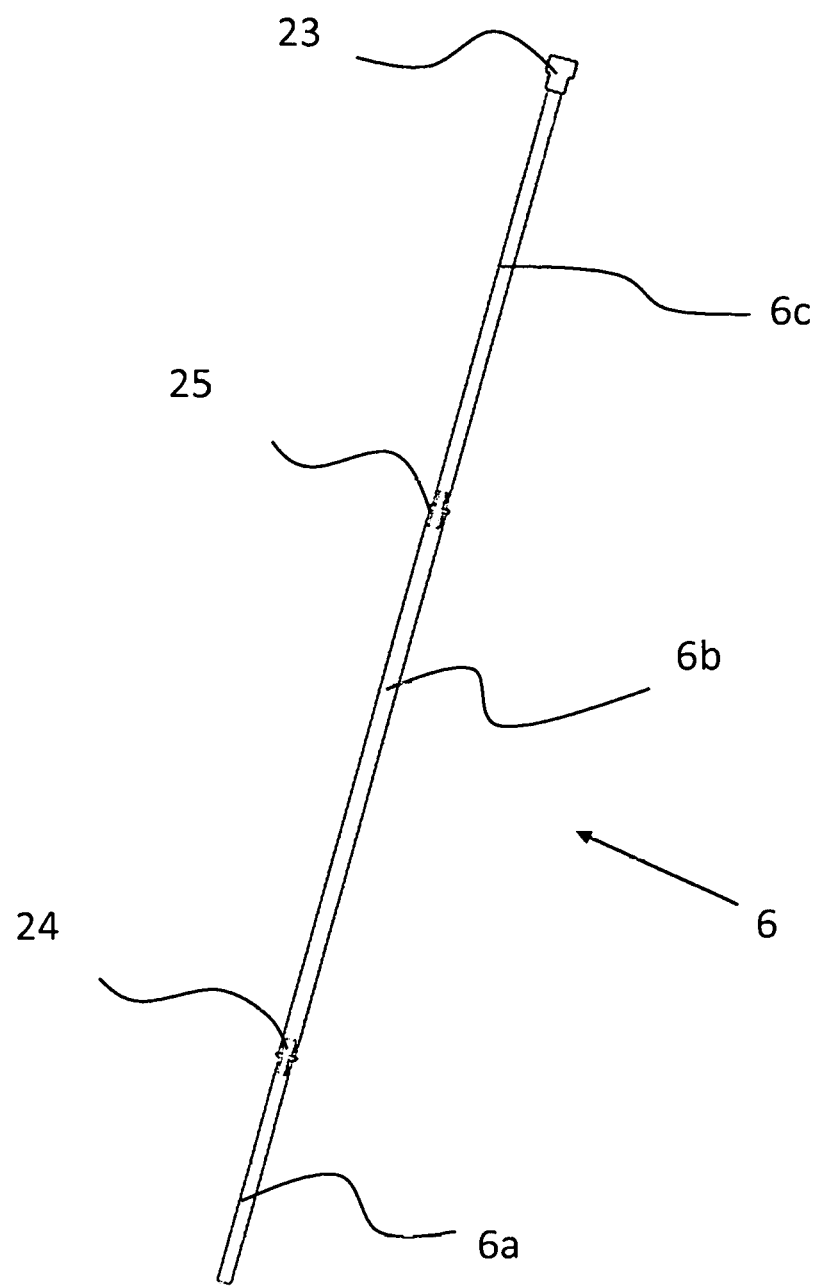
Figure 13:
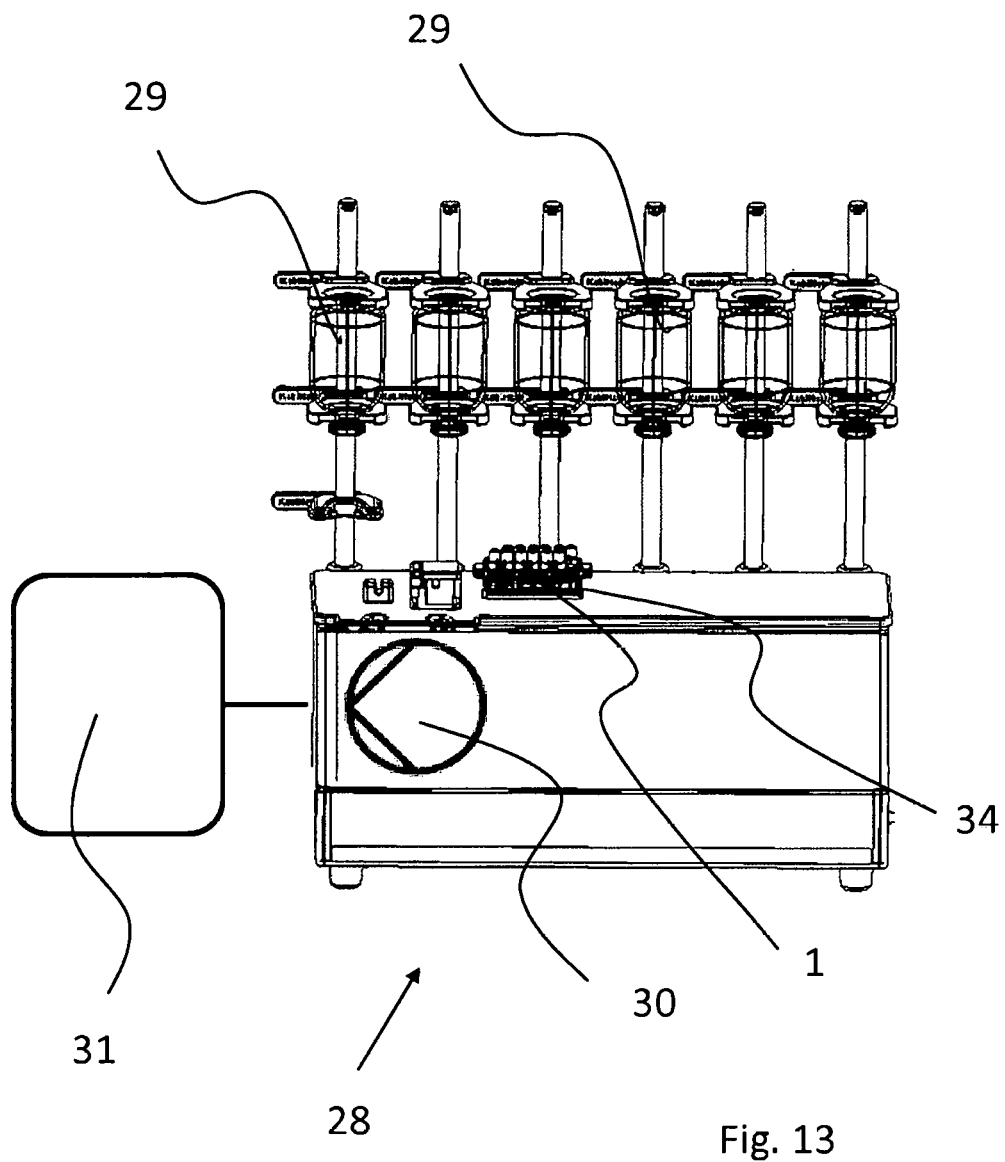
Figure 14:
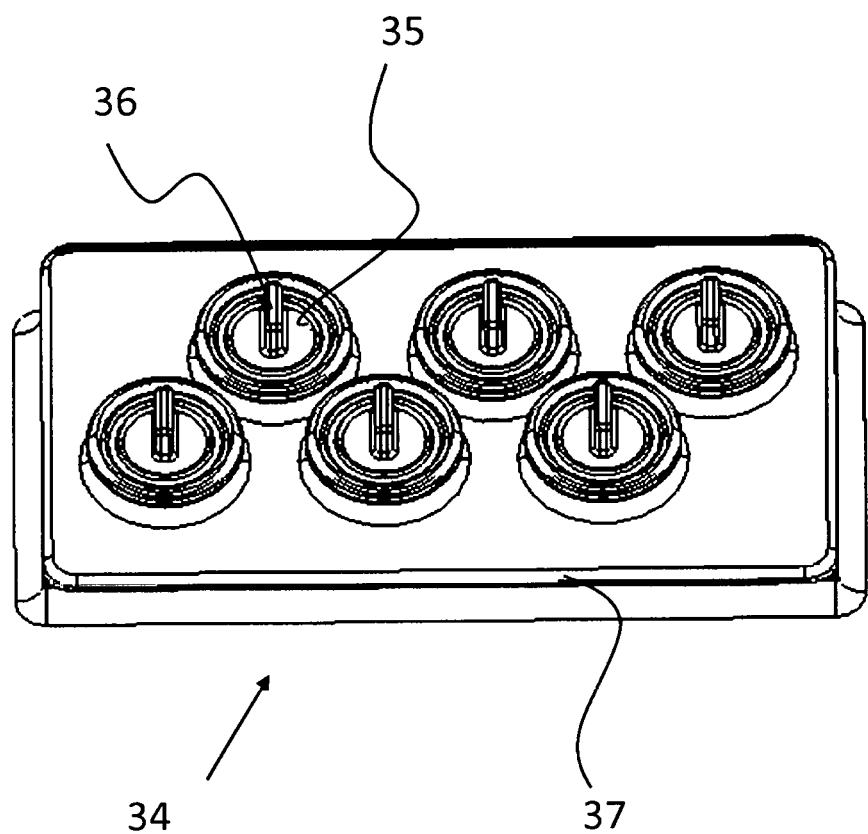

FIG. 9 shows a detailed illustration of the plug of the valve;

FIG. 10 shows a section through the plug that runs perpendicularly to the axis of main extent;

FIG. 11 shows a detailed illustration of the connector pieces for the source containers;

FIG. 12 shows a detailed illustration of the hose of the outflow of the valve unit;

FIG. 13 shows a schematic illustration of an installation for producing a medical preparation; and FIG. 14 shows a perspective view onto the receptacle on the installation for a valve unit according to the invention.

DETAILED DESCRIPTION OF THE DRAWINGS

Figure 1:
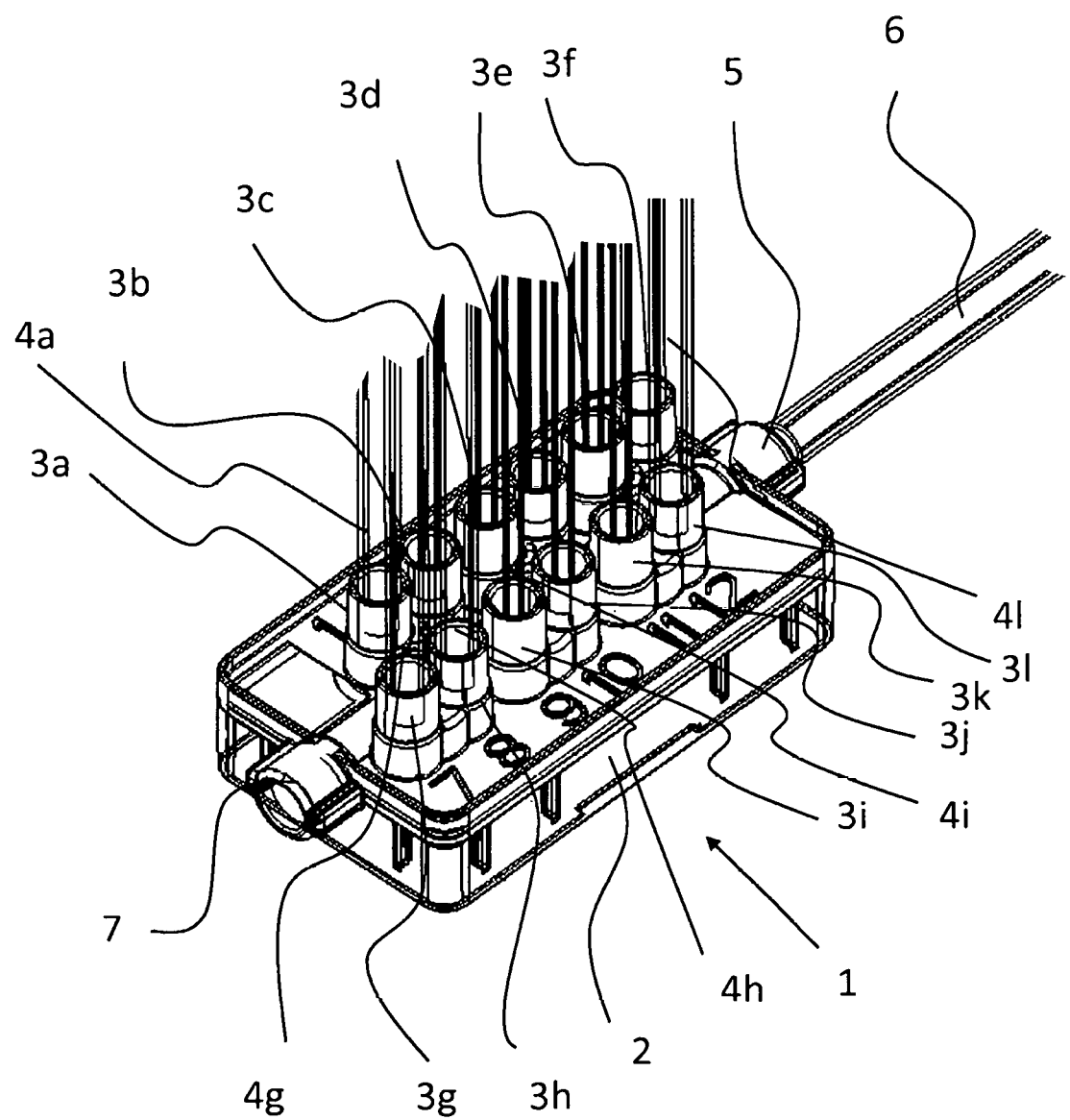
FIG. 1 shows a perspective wireframe illustration of a valve unit according to the invention.

FIG. 1 in a perspective illustration shows an embodiment of a valve unit 1 which is configured as a single-use component.

The valve unit 1 comprises a housing 2 from a plastics material. Said housing can be configured in the manner of a cartridge.

The housing 2 that is configured in the shape of a cuboid on the upper side thereof comprises a plurality of inflows 3*a*-3*l*. There are twelve inflows 3*a*-3*l* present in this exemplary embodiment. The valve unit 1 can also be configured having more or fewer inflows.

The housing 2 preferably has a height of 2 to 6 cm, a width of 6 to 12 cm, and a depth of 3 to 8 cm.

In each case two inflows, the inflows 3*a* and 3*b* and the inflows 3*c* and 3*d* in this exemplary embodiment, are opened and closed by way of in each case one single 3-way valve 9.

The variant of embodiment of a valve unit 1 illustrated here comprises six 3-way valves. Each inflow 3*a*-3*l* is connected to one flexible hose 4*a*-4*l*. For improved clarity, the hoses 4*a*-4*l* in this view are only in part provided with reference signs, but correspond to the inflows 3*a*-3*l*, that is to say that one hose 4*a*-4*l* is assigned to each inflow 3*a*-3*l*.

The hoses 4*a*-4*l* are connected, preferably welded or adhesively bonded, to the inflows 3*a*-3*l* in such a manner that said hoses 4*a*-4*l* cannot be released in a non-destructive manner.

In this exemplary embodiment, for example the hoses 4h and 4i have a diameter that is smaller than that of the hoses 4a and 4l. The hoses 4h and 4i serve for metering microquantities.

A target container (not illustrated) can be filled by way of an outflow 5 and a hose 6 to which the outflow 5 is preferably likewise inseparably connected.

Only that end of the hose 4a-4l, 6 that points toward the respective connector of the housing 2 is illustrated in this illustration, but not the remaining parts of the hoses that have the connectors (cf. FIG. 11 and FIG. 12).

In this exemplary embodiment a further connector 7 is provided on the side opposite the outflow 5. The valve unit 1 can be closed from both sides by way of the connector 7. An outflow 5 or connector 7, respectively, that is not required can be readily closed.

Figure 2:
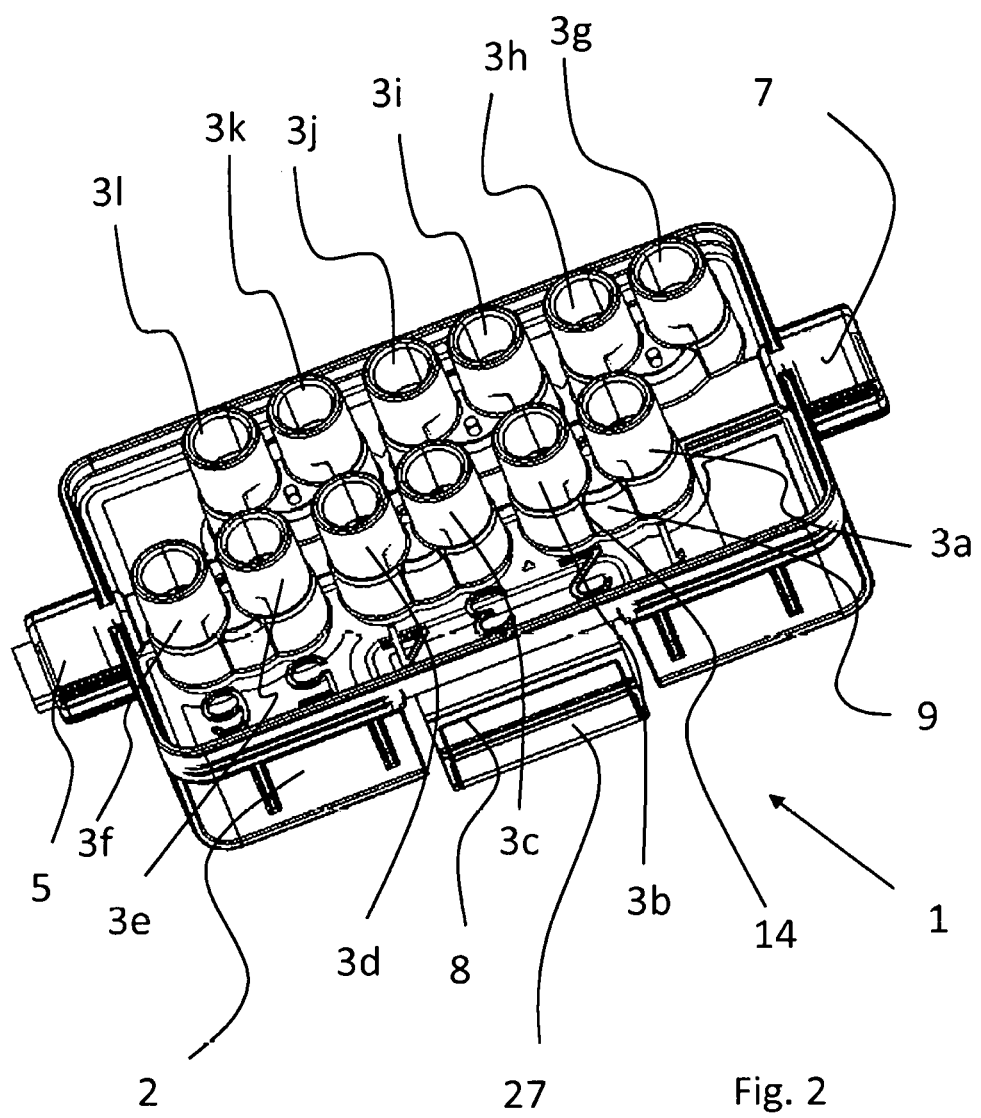
FIG. 2 shows a perspective view of the valve unit without hoses.

FIG. 2 shows a perspective view of the housing 2 of the valve unit 1, in which the hoses 4a to 4l for the inflows 3a to 3l and for the outflow 5 have been omitted. The view has been rotated by approx. 180° in relation to that of FIG. 1.

The latching hook 8, in order for the valve unit 1 to be able to be latched onto the top of an installation 28, can be seen in particular in this illustration. The housing 2 on the opposite side is held by a collar 26 that engages below a form-fitting element on the installation (cf. also FIG. 3).

In order for the valve unit 1 to be removed, the user only has to pull from the front the handle 27 of the sprung latching hook 8 upward, this releasing the latching mechanism, so that the valve unit 1 can be removed.

Furthermore to be seen are the valves 9. The valve housing 14 of the valves 9 protrudes from the upper side of the housing 2. Only one valve 9 is marked with a reference sign in the figure.

The valves 9 for in each case two inflows 3a-3l are preferably of identical configuration such that the description hereunder of a valve 9 refers to all of the valves 9 of the valve unit 1.

The valve 9, identified here by the reference sign 9, serves for actuating the inflows 3a and 3b. The inflows 3a and 3b in the plan view of the upper side of the valve unit 1 overlap with the valve housing 14. The inflows 3a to 3l can thus be placed close to one another. At the same time, a duct from the respective inflow 3a, 3b can be readily provided by way of an opening (15a, 15b in FIG. 4) in the overlap region of the inflows 3a, 3b and of the valve housing 14.

The valve housing 14 has an internal diameter that is preferably 1.1 to 1.5 times that of the inflow 3a, 3b. The valve housing 14 has an internal diameter of 0.5 to 2 cm, for example.

The inflows 3a, 3b above the valve housing 14 are preferably spaced apart by less than half of the external diameter of said inflows 3a, 3b.

Figure 3:
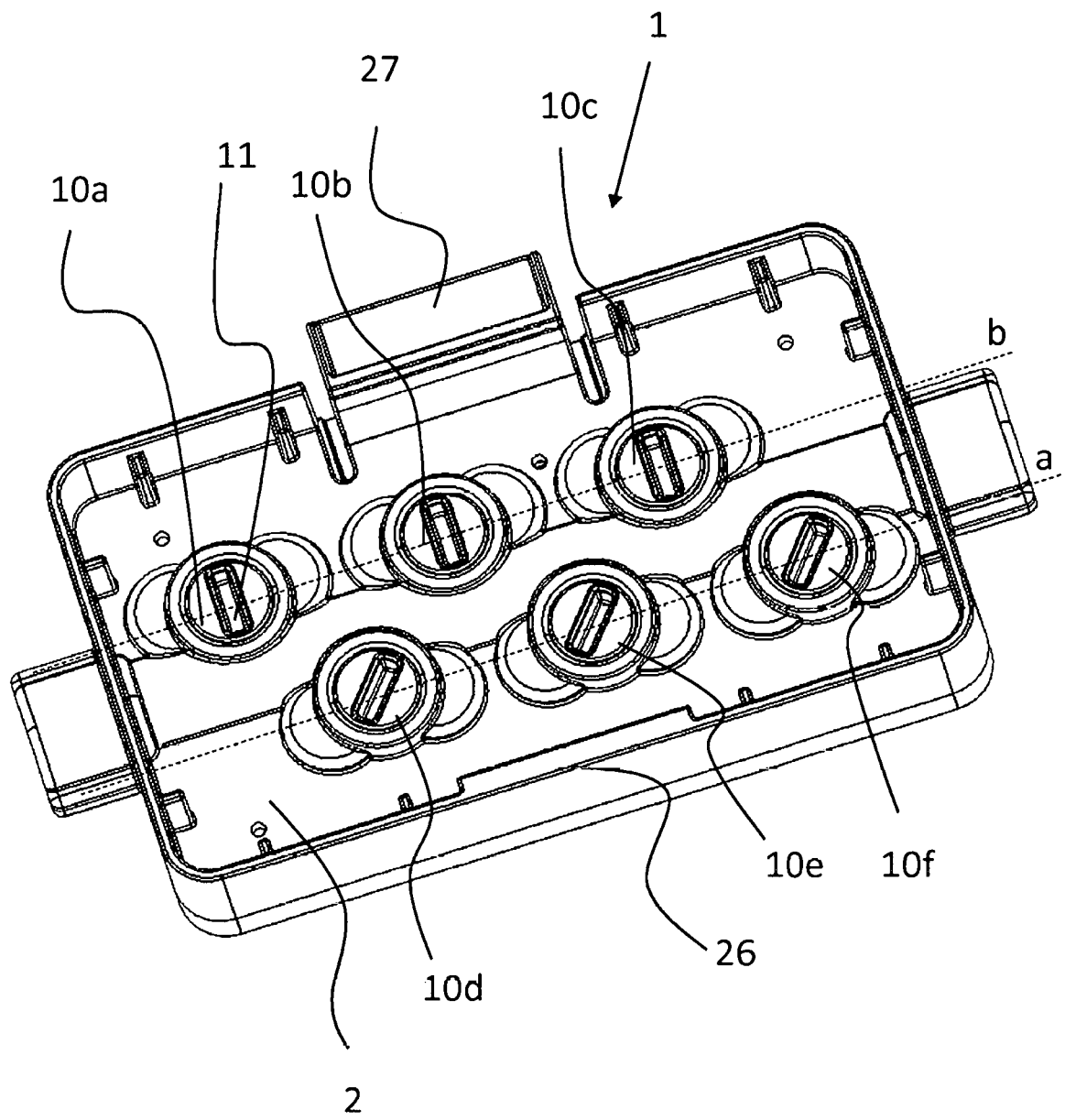
FIG. 3 shows a view onto the lower side of the valve unit.

FIG. 3 shows a perspective view onto the lower side of the housing 2.

The valves 9 have in each case one press-fitted plug 10a-10f which comprises a slot 11 which serves as an engagement element for a drive that is activated by means of a motor (cf. to this end the entrainment elements 35 having the engagement elements 36 in FIG. 14).

The complete opening of an inflow 3a-3l is performed by approximately a quarter rotation, preferably an eighth of a rotation, of the plug 10a-10f, wherein the one connector is opened by the rotating in one direction, and the other connector is opened by the rotating in the other direction. The rotation for achieving the two opening positions is thus established substantially by +/−45° in relation to the closed central position.

3/3-way valves having a closed central position are thus used.

The plugs 10a-10f in a plan view are disposed in the two straight rows a and b, wherein the plugs 10d-10f of row a in relation to the plugs 10a-10c of row b are axially offset in relation to the respective opposite plugs.

The plugs 10a-10c of row b are in the central position, the respective valves 9 thus being closed. The plugs 10c-10e of row a by contrast are rotated by an eighth of a rotation, in each case one inflow (3a to 3l) being open. However, it is understood that in the operation of the installation 28 for producing a medical preparation only one valve 9 is opened at any one time during a metering step. In detail, the valve 9 in this instance is open only in relation to one inflow of the inflows 3a to 3l.

Figure 4:
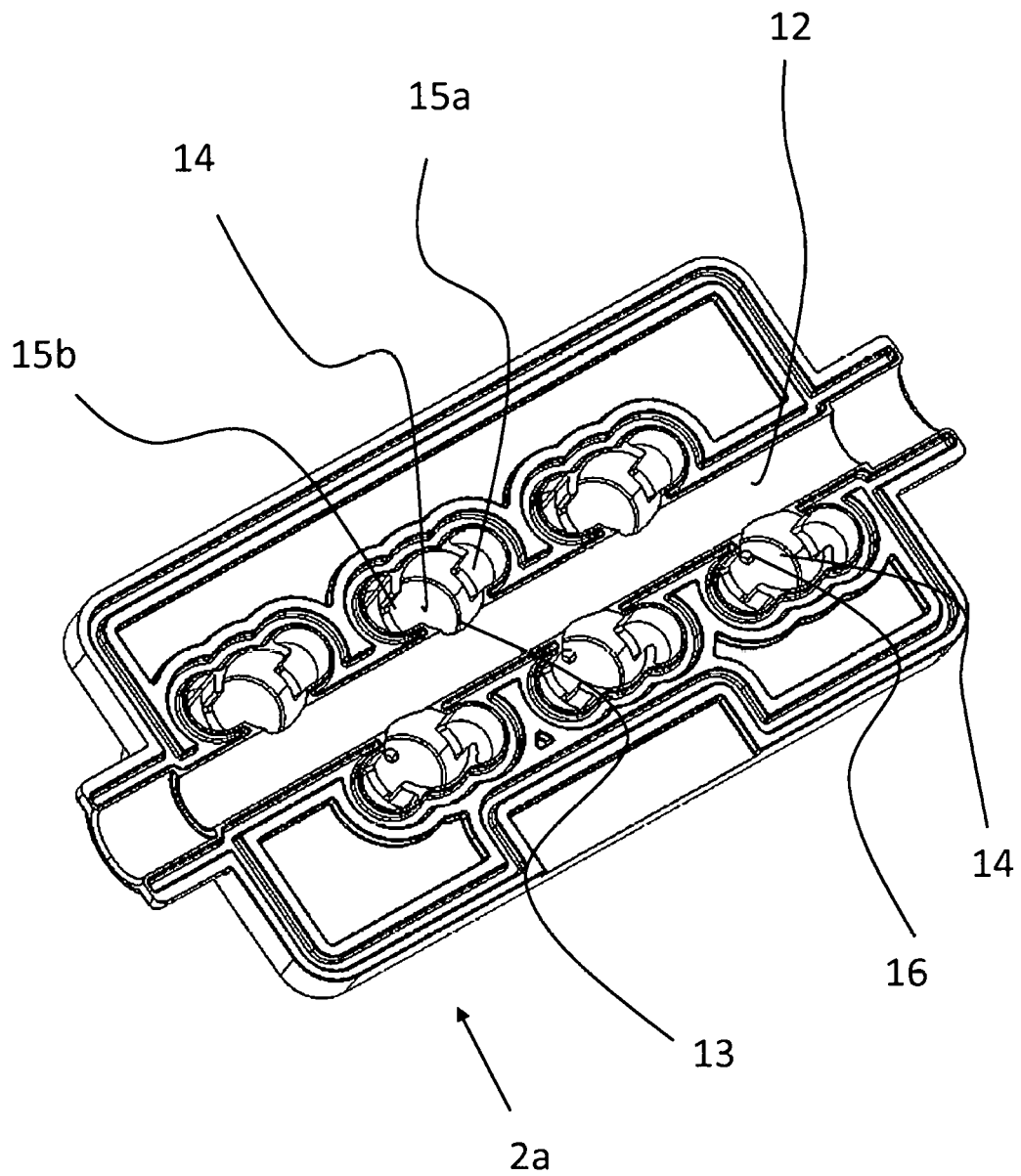
FIG. 4 shows a view onto the lower side of a housing upper part.

FIG. 4 shows the illustration of a housing upper part 2a of the housing 2 without the plugs 9. The exemplary embodiment illustrated here thus shows a housing 2 in two parts. The housing 2 in the case of another embodiment is configured integrally, but otherwise in a manner analogous to the exemplary embodiment illustrated here.

It can be seen that the valve housings 14 are formed substantially by a preferably circular-cylindrically shaped duct in the housing 2 which from the lower side of the housing 2 leads into the housing 2. The plugs 10 are press-fitted into the housing 2 by way of the lower side of the housing 2.

Each valve housing 14 laterally comprises an opening 15a, 15b which in each case leads to the inflow 3a-3l at the valve.

In two opened positions of the plug 10 a fluid can pass the plug 10 either from the one inflow by way of the opening 15a or from the other inflow by way of the opening 15b, and make its way out of the valve housing 14 into a central duct 12 by way of the opening 13.

Figure 6:
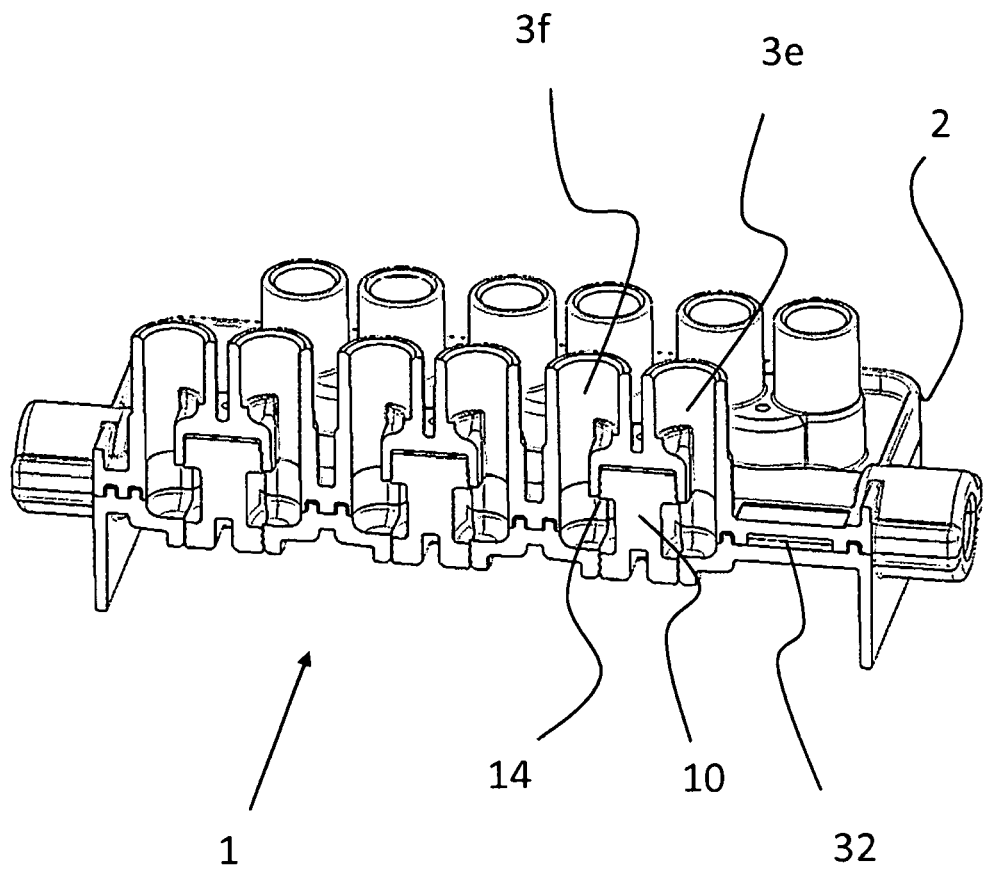
FIG. 6 shows a sectional perspective view of the valve unit.

The openings 15a, 15b in this exemplary embodiment are configured so as to be substantially slot-shaped and are level in height with a clearance 10 of the plug 10 (cf. FIG. 6).

The circular-cylindrical shape of the valve housing 14 overlaps the duct 12. The opening 13 of the valve housing 14 thus formed opens into the duct 12. The fluid can flow into the duct 12 by way of the opening 13.

The duct 12, preferably at least in the region of the valves 9, has a consistent cross section. This ensures openings 13 of identical size in the case of all valves 9 which in turn guarantees approximately identical flow rates of all valves 9 in the opened state.

The openings 15a, 15b can be implemented by way of two housing halves that are joined together, as is illustrated here.

The valve housing 14 on the upper side has a ventilation hole 16. The air present in the valve housing 14 can flow out by way of the ventilation hole 16 when the plug 10 is being press-fitted.

Figure 5:
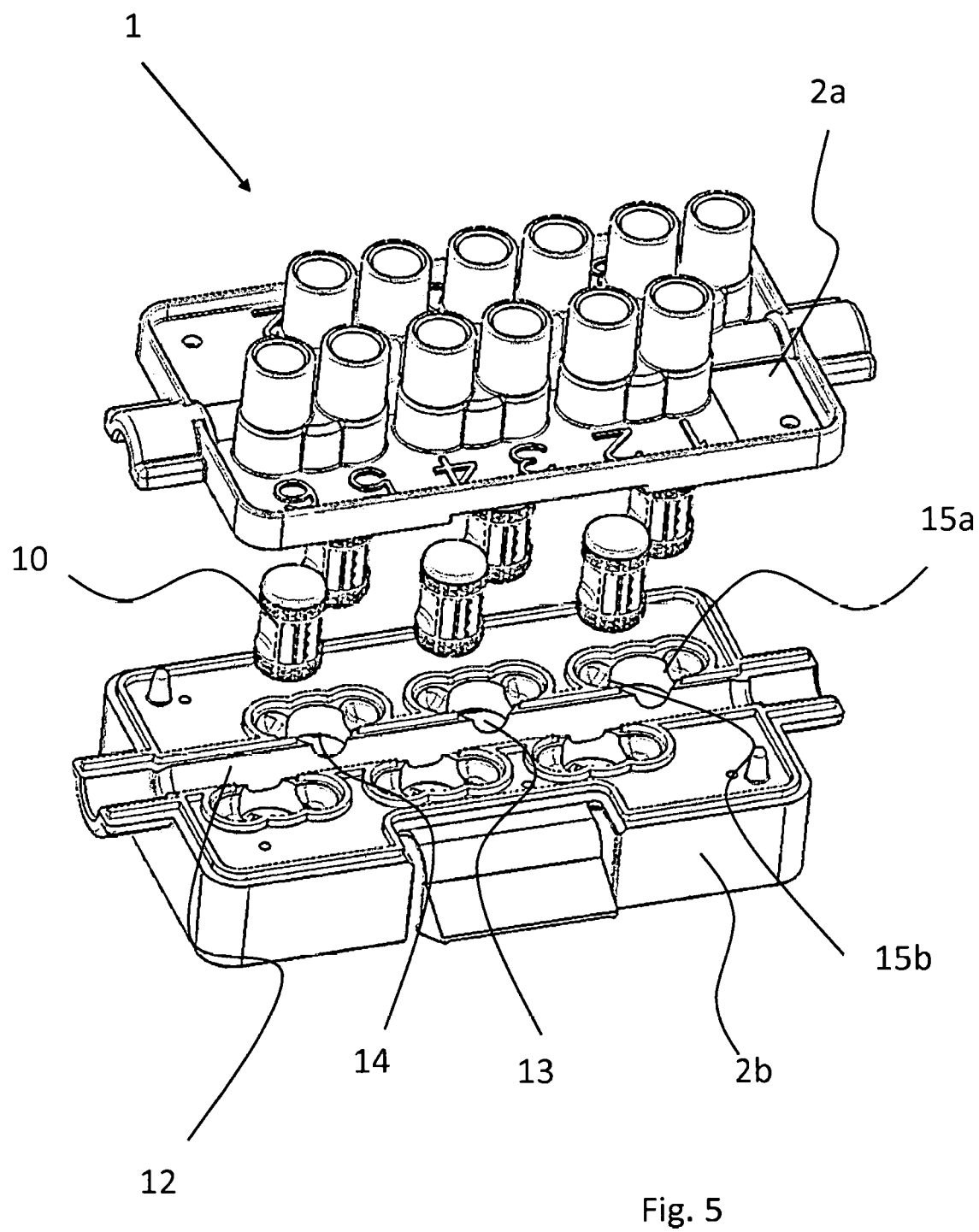
FIG. 5 shows an exploded illustration of the valve unit.

FIG. 5 shows an exploded illustration of the valve unit 1 which here is in two parts. The housing 2 comprises a housing upper part 2a and a housing lower part 2b.

The lower part of the circular-cylindrically-shaped valve housing 14 for receiving the plugs 10 can now be seen. The valve housing 14 opens into the central duct 12 by way of in each case one opening 13.

Furthermore to be seen are the openings 15a and 15b which lead to the inflows 3a-3l.

FIG. 6 shows a view that is in section along the direction of main extent of the valve unit 1.

The plugs 10 that are press-fitted into the valve housing 14 can be seen. The inflow 3e or the inflow 3f can be connected to the central duct 12 of the valve unit 1 by way of the plug identified by the reference sign 10.

It can furthermore be seen that the housing 2 comprises a plate 32 which serves as a support for the valves 9.

The plate 32 in this exemplary embodiment is configured in two tiers since the housing 2 is embodied in two parts. In an alternative integral embodiment of the housing 2 (not illustrated here) the plate 32 would be in one tier.

Figure 7A:
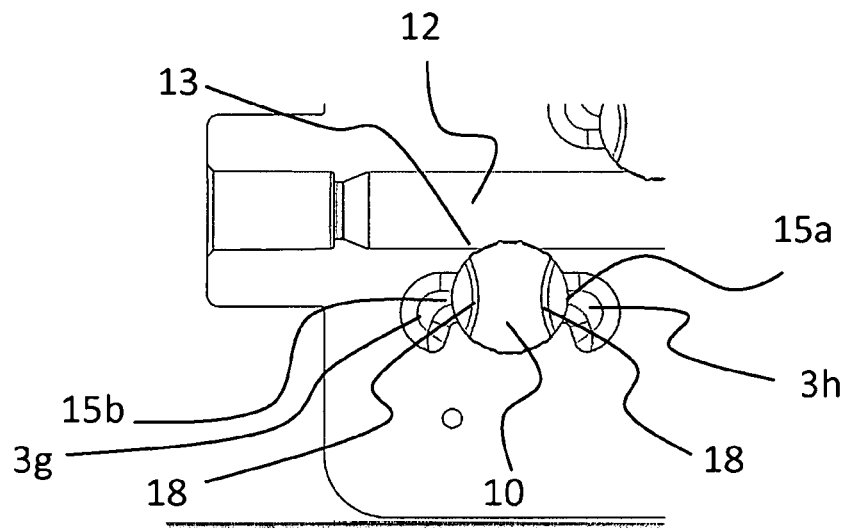
Figure 7B:
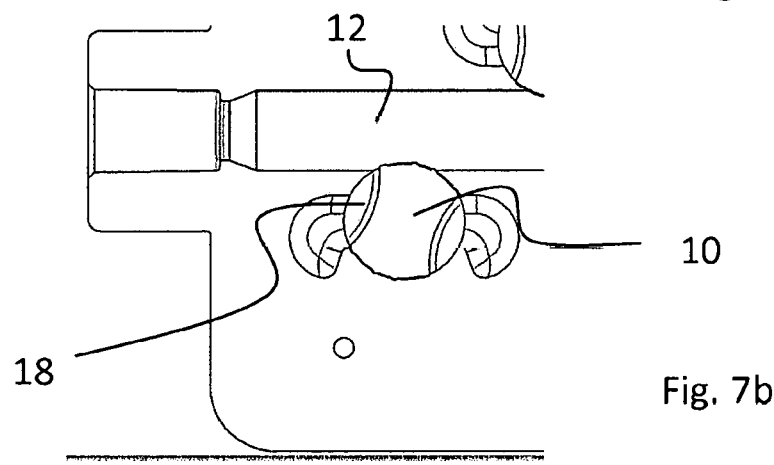
Figure 7C:
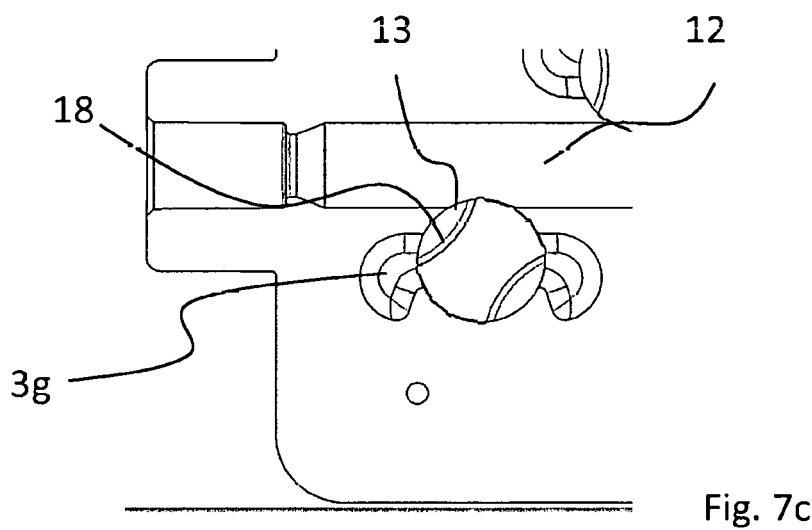

FIGS. 7a to 7c show sectional views of a valve 9 in various positions.

The plug 10 of the valve 9 in the view according to FIG. 7a is located in the closed central position. The opening 13 between the duct 12 and the valve housing 13 is closed by the plug 10. On account thereof, no fluid can make its way into the duct 12 by way of the inflow 3h and the opening 15a, or by way of the inflow 3g and the opening 15b, respectively.

FIG. 7b shows the valve 9 during opening. The clearance 18 on the jacket of the plug 10 reaches the opening 13 of the duct 12, and fluid can flow into the duct 12 through the opening 13.

FIG. 7c shows the valve 9 in the completely open position. A duct is released upon an eighth of a rotation, and fluid can flow into the duct 12 from the inflow 3q by way of the external face on the jacket of the plug 10 along the clearance 18 and through the opening 13.

During the operation of the installation 28, liquid can henceforth be retrieved from the source container 29 that is connected to the inflow 3g.

Figure 8A:
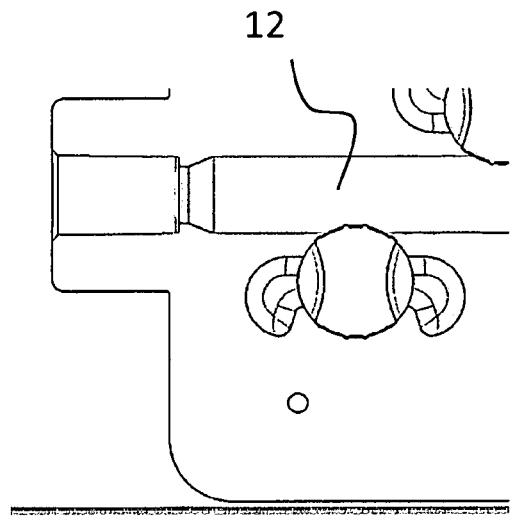
Figure 8B:
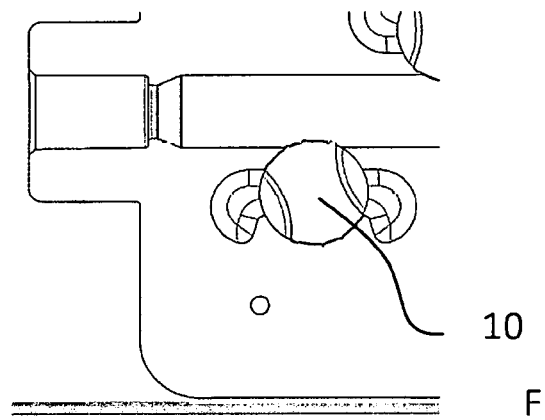
Figure 8C:
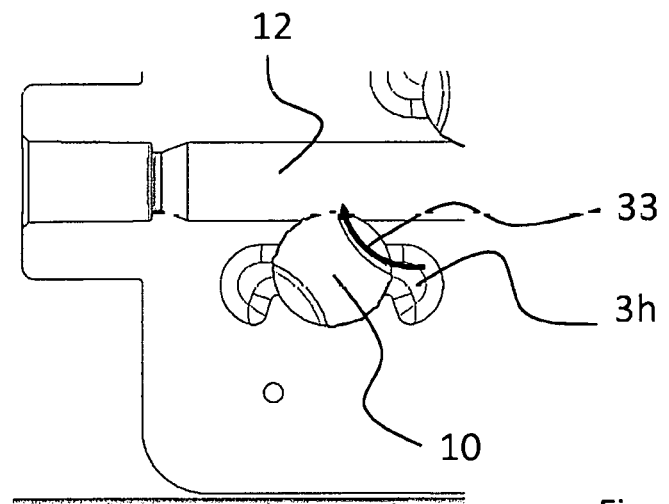

The illustration according to FIG. 8a to FIG. 8c corresponds to that of FIG. 7a to FIG. 7c, the point of differentiation being that the plug 10, proceeding from the closed central position illustrated in FIG. 8a, is rotated by an eighth of a rotation in the opposite direction.

As can be seen in FIG. 8c, the inflow 3h is henceforth connected to the duct 12. The fluid flow is symbolized by the plotted arrow 33.

FIG. 9 shows a detailed illustration of the plug 10 in a perspective wireframe illustration.

The plug 10 on the lower side thereof has a slot 11 as an engagement element for a drive (cf. to this end also FIG. 14).

The plug 10 is configured so as to be substantially circular-cylindrically shaped and is press-fitted into the valve housing 14.

The plug 10 preferably has a diameter of 0.5 to 2 cm and/or a height of 0.5 to 3 cm.

In order for a duct in the valve 9 to be released in the open state, the plug 10 comprises two mutually opposite clearances 18 (only one clearance is to be seen in this view).

The clearances 18 preferably occupy a quarter of the circumference of the plug 10 (cf. to this end FIG. 10).

In each case two regions which have the encircling and axially mutually spaced apart webs 17a-17c and 19a-19c are provided above and below the clearances 18.

The webs 19a-19c above the clearance 18 act as a lip seal, while the webs 17a-17c configure lip seals on the lower side of the housing 14, thus sealing the plug 10 on the lower side of the housing 14.

In the region in which there are no clearances 18 present, the plug 10 comprises axially running webs 20a-20d which are effective as lip seals between the opening 13 to the duct 12 and the openings 15a, 15b at the inlet side of the valve housing 14.

The outlet 15a and 15b at the valve side in the closed position is sealed, or the respective unopened inflow 3a-3l is blocked in the opened position, respectively, by way of the webs 20a-20d.

FIG. 10 (at the height level of the clearance 18) shows a radial sectional plane of the plug 10. The two mutually opposite curved clearances 18 which extend axially across a central region of the plug 10 can be seen (cf. to this end FIG. 9).

The clearances 18 occupy in each case approximately a quarter of the circumference of the jacket of the plug 10.

Furthermore to be seen are the axially running webs 20a-20d which are distributed around the jacket of the plug 10 in the region in which the clearances 18 do not extend.

FIG. 11 shows the connector pieces 21, 22 of the hoses 4a-4l of the inflows.

The connector pieces 21, 22 can be configured, for example, as a Luer lock connector and/or comprise a spike.

It can be seen that the hose 4h, for example, is shorter than the hose 4g. The hose 4h also has a smaller diameter and serves for metering micro-quantities.

FIG. 12 shows an illustration of the hose 6 for the outflow 5.

Said hose 6 comprises a connector 23 for the target container, said connector 23 potentially being configured as a Luer lock connector, for example.

The hose 6 is subdivided into the hose portions 6a-6c which are in each case connected by means of one connection piece 24, 25.

The central portion 6b has a diameter that is larger than that of the adjacent portions 6a and 6c, and serves for the use of the hose 6 in a peristaltic pump, in particular a hose pump in the design of a roller pump or a finger pump (not illustrated).

FIG. 13 shows a schematic illustration of a installation 28 for producing a medical preparation, especially for producing a preparation for parenteral nutrition. The valve unit 1 is a separate component which can be fastened on top of the installation 28. The valve unit 1 can be removed again after use and in particular be disposed of conjointly with the hoses 4a-4l and 6.

The valve unit 1 here is latched to a receptacle 34 on the upper side of the installation 28. The hoses 4a to 4l and 6 of the valve unit 1 are not illustrated. The hoses 4a to 4l of the inflows 3a to 3l are connected to the source containers 29. Only the source containers 29 for micro-quantities, provided in exemplary manner by vials, are illustrated here.

The hose 6 of the outflow 5 is connected to a target container (not illustrated) which is placed onto a balance 31 which is connected to the installation 28.

A patient-specific preparation can be transferred to the target container in a computer-controlled manner by way of a pump 30, wherein it is controlled by way of the valves 9 of the valve unit 1 from which source container 29 liquid is retrieved. The retrieved quantity can be checked by way of the balance 31.

FIG. 14 shows a perspective detailed illustration of the receptacle 34 on the installation for the valve unit 1.

The receptacle 34 comprises a protruding periphery 37 which serves as a form-fitting element for the latching hook 8 as well as for the collar 26 of the valve unit 1.

The receptacle 34 furthermore comprises entrainment elements 35 which can be rotated by means of a motor on the installation.

The entrainment elements 35, in a manner corresponding to that of the plugs 10, are disposed in two straight rows, wherein the entrainment elements 35 of the one row are axially offset in relation to the entrainment elements 35 of the other row.

The entrainment elements 35 comprise engagement elements 36 which are configured in the manner of a screwdriver and which in the latched state of the valve unit 1 engage in the slots 11 of the plugs 10. The plugs 10 can thus be rotated and the valves 9 can be activated by way of the entrainment elements 35.

A robust and reliable valve unit for a installation for preparing parenteral nutrition can be provided by the invention.

LIST OF REFERENCE SIGNS

1 Valve unit
2 Housing
2a Housing upper part
2b Housing lower part
3a-3l Inflow
4a-4l Hose
5 Outflow
6 Hose
6a-6c Hose portion
7 Connector
8 Latching hook
9 Valve
10, 10a-10f Plugs
11 Slot
12 Duct
13 Opening
14 Valve housing
15a, 15b Opening
16 Ventilation hole
17a-17c Web
18 Clearance
19a-19c Web
20a-20d Web
21 Connector
22 Connector
23 Connector
24 Connection piece
25 Connection piece
26 Collar
27 Handle
28 Installation
29 Source container
30 Pump
31 Balance
32 Plate
33 Arrow
34 Receptacle
35 Entrainment element
36 Engagement element
37 Periphery

The invention claimed is:

1. A valve unit for an installation for producing a medical for parenteral nutrition, said valve unit comprising a cartridge having a plurality of inflows and an outflow, wherein the inflows are connectable to the outflow by way of valves, wherein the valves are each configured as at least 3-way valves that connect to at least two of said inflows and to said outflow such that first and second source containers can be connected to a single valve; and wherein each of said valves comprises a valve member that is rotatable about a valve axis, and wherein said valve member rotates between a first position and a second position, wherein, in said first position, said valve member connects said first source container to said outflow, and wherein, in said second position, said valve member connects said second source container to said outflow, wherein the valve axis is offset and perpendicular to an outflow axis.

2. The valve unit as claimed claim 1, wherein the outflow is connected to a duct that is disposed in the cartridge, wherein the duct has openings that, laterally, lead to the valves.

3. The valve unit as claimed in claim 2, wherein the valves are configured as 3/3-way valves having a blocked central position.

4. The valve unit as claimed in claim 1, wherein the valves are disposed in at least two straight rows, wherein the valves of one row are disposed so as to be offset in the axial direction in relation to the valves in the other row.

5. The valve unit as claimed in claim 4, wherein the duct at least in the region of the valves has a constant diameter.

6. The valve unit as claimed in claim 1, wherein the inflows and/or the outflow are/is inseparably connected to hoses.

7. The valve unit as claimed in claim 1, wherein the inflows are connected to hoses which are present in at least two different diameters, and/or in that the outflow is connected to a hose which comprises at least three portions, wherein a central portion has a cross section that is enlarged in relation to the adjacent portions.

8. The valve unit as claimed in 1, wherein the valve unit has at least four inflows.

9. The valve unit as claimed in claim 1, wherein the cartridge has latching means for fastening to a drive unit of the installation for producing a medical preparation.

10. The valve unit as claimed in claim 1, wherein the valve members are formed as plugs from an elastomer, said plugs being inserted into the housing cartridge in a lubricant-free manner.

11. The valve unit as claimed in claim 1, wherein the valve members are formed as plugs which on a lower side have an engagement element for a drive, said engagement element being configured as a slot.

12. The valve unit as claimed in claim 1, wherein the valve members are formed as plugs, wherein a fluid in an opened position is capable of being guided along an external face of the plugs.

13. The valve unit as claimed in claim 1, wherein the valve members are formed as plugs, and wherein the plugs comprise a clearance by way of which in an opened position of the valve a duct is configured between an inflow and the outflow of the valve, and/or in that the plugs are composed of an elastomer and have at least one encircling web above and below the clearance, said web acting as a seal in relation to the housing.

14. An installation for producing a medical preparation for producing parenteral nutrition, comprising a valve unit as claimed in claim 1.

15. The valve unit as claimed in claim 1, wherein the valve unit has at least eight inflows.

16. The valve unit as claimed in claim 1, wherein the valve unit has at least twelve inflows.

17. The valve unit as claimed in claim 1, wherein the valve members are formed as plugs, and wherein the plugs comprise two clearances, by way of which in an opened position of the valve a duct is configured between an inflow and the outflow of the valve, and/or in that the plugs are composed of an elastomer and have at least one encircling web above and below the clearance, said web acting as a seal in relation to the cartridge.

18. The valve unit as claimed in claim 1, in which the cartridge is an injection-molded component.

19. A valve unit for an installation for producing a medical preparation for parenteral nutrition, comprising a housing having a plurality of inflows and an outflow wherein the inflows are connectable to the outflow by way of valves, wherein the inflows are in each case connected to a hose, wherein the hoses are inseparably connected to the housing; and wherein each of said valves rotates about an axis that is offset from and perpendicular to an axis of said outflow, wherein said inflows comprise, for each valve, a first and second inflow, wherein each of said valves rotates between a first position and a second position, wherein, in said first position, said valve connects said first inflow to said outflow, and wherein in said second position, said valve connects said second inflow to said outflow.

* * * * *